United States Patent
Hoveyda et al.

(10) Patent No.: US 11,332,426 B2
(45) Date of Patent: May 17, 2022

(54) METHOD OF PREPARING TRISUBSTITUTED ETHYLENE COMPOUNDS

(71) Applicants: Trustees of Boston College, Chestnut Hill, MA (US); Massachusetts Institute of Technology, Cambridge, MA (US)

(72) Inventors: Amir H. Hoveyda, Lincoln, MA (US); Thach T. Nguyen, Newton, MA (US); Ming Joo Koh, Chestnut Hill, MA (US); Chaofan Xu, Brighton, MA (US); Sebastian Torker, Brighton, MA (US); Richard Royce Schrock, Winchester, MA (US)

(73) Assignees: Trustees of Boston College, Chestnut Hill, MA (US); Massachusetts Institute of Technology, Cambridge, MA (US)

( * ) Notice: Subject to any disclaimer, the term of this patent is extended or adjusted under 35 U.S.C. 154(b) by 254 days.

(21) Appl. No.: 16/646,479

(22) PCT Filed: Sep. 21, 2018

(86) PCT No.: PCT/US2018/052252
§ 371 (c)(1),
(2) Date: Mar. 11, 2020

(87) PCT Pub. No.: WO2019/060749
PCT Pub. Date: Mar. 28, 2019

(65) Prior Publication Data
US 2020/0270194 A1    Aug. 27, 2020

Related U.S. Application Data

(60) Provisional application No. 62/562,224, filed on Sep. 22, 2017.

(51) Int. Cl.
| | | |
|---|---|---|
| *C07C 41/30* | (2006.01) | |
| *B01J 31/22* | (2006.01) | |
| *C07C 43/178* | (2006.01) | |
| *C07C 2/04* | (2006.01) | |
| *C07C 6/04* | (2006.01) | |
| *C07C 6/02* | (2006.01) | |

(52) U.S. Cl.
CPC .......... *C07C 41/30* (2013.01); *B01J 31/2273* (2013.01); *C07C 2/04* (2013.01); *C07C 6/02* (2013.01); *C07C 6/04* (2013.01); *C07C 43/1787* (2013.01); *B01J 2231/543* (2013.01); *B01J 2531/821* (2013.01)

(58) Field of Classification Search
CPC .. C07C 41/30; C07C 2/04; C07C 6/02; C07C 6/04; C07C 43/1787; C07C 17/00; C07C 1/321; C07C 67/343; B01J 31/2273; B01J 2231/543; B01J 2531/821; B01J 2540/20; B01J 31/1805; B01J 31/181; B01J 31/2208; B01J 31/2226; B01J 31/226; B01J 31/2265; B01J 31/2278; B01J 2531/64; Y02P 20/52; C07F 15/0046
See application file for complete search history.

(56) References Cited

U.S. PATENT DOCUMENTS 7,723,255 B2    5/2010    Hoveyda et al.

FOREIGN PATENT DOCUMENTS

| WO | 2014139679 | 9/2014 |
|---|---|---|
| WO | 2014201300 | 12/2014 |

OTHER PUBLICATIONS

International Search Report and Written Opinion dated Jan. 24, 2019 for international application PCT/US2018/052252.
Chatterjee, et al., "Synthesis of Symmetrical Trisubstituted Olefins by Cross Metathesis", Organic Letters, 2002, vol. 4, No. 11, pp. 1939-1942.
Chatterjee, et al., "Synthesis of Trisubstituted alkenes via Olefin Cross-Metathesis", Organic Letters, 1999, vol. 1, No. 11, pp. 1751-1753.
Corey, et al., "The Application of the Shapiro Reaction to the Stereoselective Synthesis of E-Trisubstituted Olefins for Cation-Olefin Cyclization by Three Component Coupling", Tetrahedron Letters 38, 8915-8918 (1997).
Hodgson, et al., "Convergent and Stereoselective Synthesis of Trisubstituted E-Alkenyl Bromides and Iodides via S-Oxido Phosponium Ylilledes", J. Am. Chem. Soc. 130, 16500-16501 (2008).

(Continued)

*Primary Examiner* — Ali Z Fadhel
(74) *Attorney, Agent, or Firm* — Stoel Rives LLP

(57) ABSTRACT

Method of forming a trisubstituted ethylene compound, the method comprising: (A) providing a trisubstituted ethylene compound bearing a first, a second and a third substituent, in which the first and the second substituent are bound to the one olefinic carbon atom and are different from one another; (B) providing a monosubstituted ethylene compound or a disubstituted ethylene compound in which the substituents are vicinally bound to the olefinic carbon atoms, bearing at least a fourth substituent, respectively; (C) subjecting the trisubstituted ethylene compound provided in step (A) to a cross-metathesis reaction with olefin provided in step (B) to form said trisubstituted ethylene, wherein the cross-metathesis reaction is catalysed by a transition metal complex bearing ligands from which one ligand is a carbene ligand, wherein the carbene complex is characterized by a M=C moiety, wherein M is the transition metal; and wherein the reaction proceeds stereoselectively.

19 Claims, No Drawings

(56) References Cited

OTHER PUBLICATIONS

Koh, et al., "Direct Synthesis of Z-alkenyl Halides Through Catalytic Cross-Metathesis", Nature, 2016, vol. 531, pp. 459-465.
Nguyen, et al., "Kinetically Controlled E-Selective Catalytic Olefin Metathesis", Science, Apr. 29, 2016, vol. 352 Issue 6285, p. 569-575.
Nguyen, et al., "Synthesis of E- and Z-trisubstituted alkenes by catalytic cross-metathesis", Nature, [published] Dec. 20, 2017, vol. 552, pp. 347-354.
Ohmura, et al., "Palladium-catalysed cis- and trans-silaboration of terminal alkynes: complementary access to stereo-defined trisubstituted alkenes", Chem. Commun. 1416-1418 (2008).
Paek, "Synthesis of Tetrasubstituted Alkenes via Metathesis", Molecules, 2012, vol. 17, pp. 3348-3358.
Tan, et al., "Widely Applicable Pd-Catalyzed trans-Selective Monoalkylation of Unactivated 1,1-Dichloro-1-alkenes and Pd-Catalyzed Second Substitution for the Selective Synthesis of E or Z Trisubstituted Alkenes", Angew. Chem. Int Ed. 45, 762-765 (2006).
European Search Report dated Apr. 26, 2021 for EP application 18859637.3.
Luo, et al., "Z-Selective Cross-Metathesis and Homodimerization of 3E-1, 3-Dienes: Reaction Optimization, Computational Analysis, and Synthetic Applications", Journal of the American Chemical Society, vol. 138, No. 42, Oct. 26, 2016 (Oct. 26, 2016) pp. 14039-14046.
Wang, et al., "An Efficient Protocol for the Cross-Metathesis of Sterically Demanding Olefins", Organic Letters, vol. 15, No. 12, Jun. 21, 2013 (Jun. 21, 2013) pp. 3006-3009.

METHOD OF PREPARING TRISUBSTITUTED ETHYLENE COMPOUNDS

CROSS-REFERENCE TO RELATED APPLICATIONS

This patent application is the U.S. National Stage filing under 35 U.S.C. 371 of International Patent Application No. PCT/US2018/052252 entitled "METHOD OF PREPARING TRISUBSTITUTED ETHYLENE COMPOUNDS," filed Sep. 21, 2018, which claims priority to U.S. Provisional Patent Application No. 62/562,224, entitled "METHOD OF PREPARING TRISUBSTITUTED ETHYLENE COMPOUNDS," filed Sep. 22, 2017, each of which is incorporated herein by reference in its entirety.

STATEMENT REGARDING FEDERALLY SPONSORED RESEARCH OR DEVELOPMENT

This invention was made with government support under Grant No. GM-59426 awarded by the National Institute of Health and Grant No. CHE-1362763 awarded by the National Science Foundation. The government has certain rights in the invention.

FIELD OF THE INVENTION

The invention is in the field of preparing trisubstituted ethylene compounds using cross-metathesis reactions. The method allows the selective provision of E- or Z-olefins.

BACKGROUND OF THE INVENTION

E- and Z-trisubstituted olefins occur widely in nature. They are used commonly in chemical synthesis such as catalytic diastereoselective and/or enantioselective hydrogenations, olefin isomerization, allylic substitution or conjugate additions.

Although catalytic cross-metathesis can, in principle, offer the possibility of a distinct, flexible and broadly applicable approach for stereoselective synthesis of alkenes, there are just a small number of reports regarding synthesis of trisubstituted alkenes by cross-metathesis.

Org. Lett., 1999, 1 (11), pp 1751-1753, discloses the synthesis of trisubstituted alkenes via olefin cross-metathesis between a geminal disubstituted olefin and a monosubstituted olefin using a 1,3-dimesityl-4,5-dihydroimidazol-2-ylidene ruthenium dichloro benzylidene complex as catalyst. The trisubstituted olefin is obtained in good yields but can only afford one of the two isomers (E) and in no more than moderate stereoselectivity.

Org. Lett., 2013, 15 (12), pp 3006-3009, discloses the synthesis of trisubstituted alkenes via olefin cross-metathesis between a geminal disubstituted olefin and a trisubstituted olefin using a 1,3-dimesityl-4,5-dihydroimidazol-2-ylidene ruthenium dichloro o-isopropyloxibenzylidene complex as catalyst.

Org. Lett., 2002, 4 (11), pp 1939-1942, discloses the synthesis of a trisubstituted olefins by cross-metathesis between a symmetrically 1,1-disubstituted olefin or a trisubstituted olefin in which geminal substituents are identical and α-olefins using a 1,3-dimesityl-4,5-dihydroimidazol-2-ylidene ruthenium dichloro benzylidene complex as catalyst.

Tetrahedron Lett. 45, 7733-7736 (2004) discloses the synthesis of trisubstituted vinyl boronates via ruthenium-catalyzed olefin cross-metathesis between a geminal disubstituted vinyl boronate and a monosubstituted olefin using a 1,3-dimesityl-4,5-dihydroimidazol-2-ylidene ruthenium dichloro benzylidene complex as catalyst.

OBJECTS OF THE INVENTION

It is the object of the present invention to provide a selective and broadly applicable method for preparing trisubstituted olefins, preferably either as an E- or a Z-isomer.

SUMMARY OF THE INVENTION

This object was achieved using a method, which comprises the provision of a trisubstituted ethylene compound, wherein the olefinic carbon atom bearing a single substituent is exchanged through a cross-metathesis reaction by another olefinic carbon atom bearing a substituent which is different from said single substituent. This reaction is catalyzed by a transition metal alkylidene or carbene complex. The method thus allows the introduction of a variety of substituents in addition to the already present geminal substituents in the provided trisubstituted ethylene compound.

It has been surprisingly found that the cross-metathesis reaction between a trisubstituted ethylene compound and a monosubstituted ethylene compound, respectively a 1,2-disubstituted alkene, is highly efficient as well as stereoselective: If an E-trisubstituted ethylene compound is provided as trisubstituted ethylene compound, then the trisubstituted olefin formed in the cross-metathesis reaction has also predominantly E-configuration. If a Z-trisubstituted olefin is provided as trisubstituted ethylene compound, then the trisubstituted olefin compound formed in the cross-metathesis reaction has also predominantly Z-configuration.

The method according to the invention is advantageous over an approach of forming trisubstituted ethylene compounds in which a geminal disubstituted ethylene compound is subjected to cross-metathesis with e.g. between a geminal disubstituted and a monosubstituted ethylene compound in order to introduce a further substituent into the geminal disubstituted ethylene compound. Such reaction typically requires high catalyst loading and extended reaction times and generates a mixture of Z- and E-olefins. The Z- and E-isomers will have to be separated from one another if the pure stereoisomers are desired. As is known, such separation is often difficult or even impossible, especially at an industrial scale using the typical industrial methods such as distillation due to similar boiling points of the two isomers. Moreover, homo-metathesis as a side-reaction of the educts and generation of unstable methylidene complexes may further complicate the separation and lower the yield of the desired product.

Contrary to this, according to the method of the invention, it is possible to provide an easily available trisubstituted ethylene compound having already the predetermined Z- or E-configuration—which, if necessary, can be made from commercially available olefins by the use of standard methods—and then modifying it according to the desired substitution pattern. This makes the new method extraordinarily and uniquely valuable for the chemical synthesis, in particular at an industrial scale.

The invention relates to a method of forming a trisubstituted ethylene compound, the method comprising:
(A) providing a trisubstituted ethylene compound bearing a first, a second and a third substituent, in which the first and the second substituent are bound to the one olefinic carbon atom, wherein said first and said second substituent are different from one another, and wherein said third substituent is bound to the other olefinic carbon atom;

(B) providing an olefin bearing at least a fourth substituent, which is bound to an olefinic carbon atom, wherein said fourth substituent is different from the third substituent of the trisubstituted ethylene compound provided in step (A); and wherein said olefin is a monosubstituted ethylene compound or a disubstituted ethylene compound in which the substituents are vicinally bound to the olefinic carbon atoms;

(C) subjecting the trisubstituted ethylene compound provided in step (A) to a cross-metathesis reaction with the olefin provided in step (B) to form said trisubstituted ethylene compound, wherein the formed trisubstituted ethylene compound has one olefinic carbon atom from the trisubstituted ethylene compound provided in step (A), which bears said first substituent and said second substituent, and one olefinic carbon atom from the olefin provided in step (B), which bears said fourth substituent; and wherein the cross-metathesis reaction is catalysed by a transition metal complex bearing ligands from which one ligand is a carbene ligand, wherein the metal complex is characterized by a M=C moiety, wherein M is the transition metal and C is the carbene carbon atom of the carbene ligand.

In the following, all terms in quotation marks are used in the meaning of the invention.

DETAILED DESCRIPTION OF THE INVENTION

The invention relates to a method of forming a trisubstituted ethylene compound, the method comprising:

(A) providing a trisubstituted ethylene compound bearing a first, a second and a third substituent, in which the first and the second substituent are bound to the one olefinic carbon atom, wherein said first and said second substituent are different from one another, and wherein said third substituent is bound to the other olefinic carbon atom;

(B) providing an olefin bearing at least a fourth substituent, which is bound to an olefinic carbon atom, wherein said fourth substituent is different from the third substituent of the trisubstituted ethylene compound provided in step (A); and wherein said olefin is a monosubstituted ethylene compound or a disubstituted ethylene compound in which the two substituents are vicinally bound to the olefinic carbon atoms, preferably wherein said two substituents are identical;

(C) subjecting the trisubstituted ethylene compound provided in step (A) to a cross-metathesis reaction with the olefin provided in step (B) to form said trisubstituted ethylene compound, wherein the formed trisubstituted ethylene compound has one olefinic carbon atom from the trisubstituted ethylene compound provided in step (A), which bears said first and said second substituents, and one olefinic carbon atom from the olefin provided in step (B), which bears said fourth substituent;

wherein the cross-metathesis reaction is catalysed by a transition metal complex bearing ligands from which one ligand is a carbene ligand, wherein the metal complex is characterized by a M=C moiety, wherein M is the transition metal and C is the carbene carbon atom of the carbene ligand.

The reaction may be schematically characterized by the equation

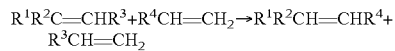

when the olefin provided in step (B) is a monosubstituted ethylene compound, and wherein $R^1$ denotes the first substituent, $R^2$ the second substituent, $R^3$ the third substituent and $R^4$ the fourth substituent.

In case of a disubstituted ethylene compound provided in step (B) in which the two substituents are identical, the reaction proceeds as follows:

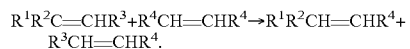

According to the invention, step (A) requires the provision of a trisubstituted ethylene compound bearing a first, a second and a third substituent, in which the first and the second substituent are bound to the one olefinic carbon atom, wherein said first and said second substituent are different from one another, and wherein said third substituent is bound to the other olefinic carbon atom.

Thus, the first and the second substituent are geminal substituents in said trisubstituted ethylene compound provided in step (A). The third substituent is a vicinal substituent relative to the first and second substituent.

Trisubstituted ethylene compounds provided in step (A) are known in the art and may be prepared according to known methods.

In a preferred embodiment, said trisubstituted ethylene compound provided in step (A) is provided in a selected stereoisomeric form, i.e. as E- or Z-isomer. Accordingly, said trisubstituted ethylene compound provided in step (A) is thus preferably prepared according to stereoselective methods. Such methods are known in the art and will be discussed in the section General Exemplification below.

According to the invention, step (B) requires the provision of an olefin bearing at least a fourth substituent, which is bound to an olefinic carbon atom, wherein said fourth substituent is different from the third substituent of the trisubstituted ethylene provided in step (A); and wherein said olefin is a monosubstituted ethylene compound or—as an alternative—a disubstituted ethylene compound in which the two substituents are vicinally bound to the olefinic carbon atoms.

In one embodiment, when said olefin is a monosubstituted olefin, a vinyl compound is provided.

In the alternative embodiment, when a disubstituted ethylene compound is provided in step (B), in which the two substituents are vicinally bound to the olefinic carbon atoms, a 1,2-disubstituted ethylene compound is provided.

This disubstituted ethylene compound may be provided in its Z- or E-configuration.

In one embodiment, said disubstituted ethylene compound is substituted with two identical fourth substituents in order to form in step (C) said trisubstituted ethylene compound.

Suitable ethylene compounds provided in step (B) are known in the art and may be prepared according to known methods.

In one embodiment, said monosubstituted ethylene compound is a vinyl halide such as vinyl chloride.

In another embodiment, said disubstituted ethylene compound is a 1,2-dihalo ethylene compound such as 1,2-dichloro ethylene.

According to the invention, the trisubstituted ethylene compound provided in step (A) is subjected in step (C) to a cross-metathesis reaction with the monosubstituted or disubstituted ethylene compound provided in step (B) to form said trisubstituted ethylene compound as the result of the cross-metathesis reaction. Herein, the formed trisubstituted ethylene compound has one olefinic carbon atom from the trisubstituted ethylene compound provided in step (A), which bears said first and said second substituents, and one olefinic carbon atom from the monosubstituted or disubstituted ethylene compound provided in step (B), which bears said fourth substituent.

The terms "first substituent", "second substituent", "third substituent" and "fourth substituent" encompass any substituent that is different from hydrogen.

The inventors of the present invention have discovered that reaction step (C) is particularly efficient, i.e. that the olefinic carbon atom bearing said third substituent in the trisubstituted ethylene compound provided in step (A) may be efficiently replaced in step (C) by said olefinic carbon atom bearing said fourth substituent provided in the monosubstituted or disubstituted ethylene compound of step (B), if said third substituent is an alkyl residue, preferably a $C_{1-4}$-alkyl residue such as a methyl group, an ethyl group, a propyl or an isopropyl group or any of the isomeric butyl groups.

In a particular preferred embodiment, said third substituent is a methyl group.

In a preferred embodiment, the first and/or second substituent and/or fourth substituent is/are a functional group or comprises/comprise a functional group.

The term "functional group" denotes any conceivable functional group. This term is further used in the commonly known meaning. i.e. a group containing e.g. halogen, nitrogen, sulfur, phosphorous or boron.

Some of the functional groups may interfere with the catalyst used in step (C). However, the person skilled in the art knows how to select an appropriate catalyst among the transition metal complexes used for catalysing such that interference may be avoided. E.g. it is known that sometimes Mo-carbene complexes are sensitive to hydroxyl groups. Then the person skilled in the art would use Ru-carbene complexes which generally tolerate hydroxyl groups.

According to the invention, the cross-metathesis reaction is catalysed by a transition metal complex bearing ligands from which at least one ligand is a carbene ligand.

The term "transition metal" encompasses a metal M selected from vanadium (V), molybdenum (Mo), tungsten (W), rhenium (Re), ruthenium (Ru) and osmium (Os).

The metals may be present in any oxidation state that suits to the metal complex bearing a carbene ligand.

In a preferred embodiment, the metal is selected from Mo, W, Re, and Ru.

In a further preferred embodiment, the metal is selected from Mo, W, and Ru.

The term "metal complex bearing a carbene ligand" encompasses a structure which has formally a metal-carbon-double bond, i.e. a M=C moiety. C represents the carbene carbon atom of the carbene ligand.

In a preferred embodiment, the carbon atom of the carbene moiety is substituted with hydrogen, or hydrogen and a residue selected from alkyl, preferably $C_{1-10}$ alkyl, optionally substituted, or aryl, preferably phenyl, optionally substituted with one or more of $C_{1-4}$ alkyl, $C_{1-4}$ alkoxy, halogen, nitro, —C(O)—N($C_{1-4}$ alkyl)$_2$, —NHC(O)($C_{1-4}$ alkyl), —S(O)$_2$—N($C_{1-4}$alkyl)$_2$ or CF$_3$.

In a preferred embodiment, the M=C moiety is selected from M=CH$_2$, M=C(H)(t-Bu), M=C(H)(CMe$_2$C$_6$H$_5$), M=C(H)(C$_6$H$_5$), M=C(H)(o-($C_{1-4}$ alkoxy)C$_6$H$_4$).

The C$_6$H$_4$ group of the M=C(H)(o-($C_{1-4}$ alkoxy)C$_6$H$_4$) moiety may be substituted with one or more of $C_{1-4}$ alkyl, $C_{1-4}$ alkoxy, halogen, nitro, —C(O)—N($C_{1-4}$ alkyl)$_2$, —S(O)$_2$—N($C_{1-4}$ alkyl)$_2$, —NHC(O)($C_{1-4}$ alkyl) or CF$_3$.

The term "carbene" is synonymously used with terms such as "alkylidene" or "arylidene" as frequently used and known in the art.

Suitable transition metal complexes bearing ligands from which at least one ligand is a carbene ligand are basically known in the art and/or may be prepared according to known methods.

Examples are e.g. aryloxy molybdenum and aryloxy tungsten carbene complexes as disclosed in WO 2014/139679 and further references mentioned therein.

Further examples are halogen or catechothiolate ruthenium carbene complexes as disclosed in e.g. U.S. Pat. No. 7,723,255 B1 and WO 2014/201300 A1.

The cross-metathesis reaction according to step (C) between the trisubstituted ethylene compound provided in step (A) and the monosubstituted or disubstituted ethylene compound provided in step (B) and catalysed by a transition metal complex bearing ligands from which one ligand is a carbene ligand may be performed by the use of reaction conditions which are basically known in the art of metathesis reactions.

The cross-metathesis reaction according to step (C) is highly stereoselective.

In one embodiment, the term "highly stereoselective" denotes that if an E-trisubstituted ethylene compound is provided as starting material in step (A), the trisubstituted ethylene compound formed in step (C) has also predominantly E-configuration.

The term "predominantly E-configuration" means that at least 60% or 70% or 80% or preferably 90% or most preferred 95% of the possible trisubstituted ethylene compounds formed in step (C) have E-configuration.

In one embodiment, the term "highly stereoselective" denotes that if a Z-trisubstituted ethylene compound is provided as starting material in step (A), the trisubstituted ethylene compound formed in step (C) has also predominantly Z-configuration.

The term "predominantly Z-configuration" means that at least 60% or 70% or 80% or preferably 90% or most preferred 95% of the possible trisubstituted ethylene compounds formed in step (C) have Z-configuration.

The terms "Z-configuration" and "E-configuration" follow the known CIP (Cahn-Ingold-Prelog) convention.

General Exemplification of the Reaction

The following general reactions exemplify the new method including methods of making the trisubstituted ethylene compound provided in step (A).

In a first approach, the trisubstituted ethylene compound provided in step (A) may be made by a cross-coupling reaction.

In one embodiment, the trisubstituted ethylene compound provided in step (A) may be made by a coupling reaction between a suitable olefin and a suitable unsaturated halide or triflate. Such reaction is known as a Heck reaction.

This reaction is typically performed in the presence of an organopalladium catalyst and a base. The halide (Br, Cl) or triflate may be an aryl, benzyl, or vinyl compound. The olefin contains at least one olefinic hydrogen and is e.g. a vinyl compound and is often electron-deficient.

The catalyst can be tetrakis(triphenylphosphine)palladium(0), palladium chloride or palladium(II) acetate. The ligand is triphenylphosphine, PHOX (a phosphiono oxazoline) or BINAP (a binaphthyl phosphorus compound). The base is triethylamine, potassium carbonate or sodium acetate.

Accordingly, said trisubstituted ethylene compound provided in step (A) is made from an unsaturated halide or triflate, which is a trisubstituted ethylene compound, in which halide or triflate and the second substituent are geminally bound to the one carbon atom of the trisubstituted ethylene compound, and a third substituent is vicinally bound to the other olefinic carbon atom.

Accordingly, step (A) comprises step (A1):

(A1) subjecting an olefin containing at least one olefinic hydrogen to cross-coupling with an unsaturated halide or triflate to afford said trisubstituted ethylene compound provided in step (A).

Herein, said unsaturated halide or triflate is a trisubstituted ethylene compound, in which two substituents form the second and the third substituent of said trisubstituted ethylene compound provided in step (A); and the first substituent of said formed trisubstituted ethylene compound provided in step (A) originates from said olefin and replaces said halide or triflate.

This cross-coupling reaction and the subsequent cross-metathesis reaction is exemplified by means of styrene

which may be reacted with commercially available (E)-2-bromo-butane in step (A1)

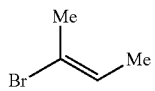

in a Heck-reaction to afford the respective trisubstituted (E)-ethylene compound (E)-(3-methylpent-3-en-1-yl)benzene

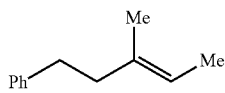 [SMILES: C/C=C(\C)CCc1ccccc1]

which is provided in step (A).

According to the invention, in step (B) an olefin bearing at least a fourth substituent, which is bound to an olefinic carbon atom, wherein said fourth substituent is different from the third substituent of the trisubstituted ethylene compound provided in step (A), and wherein said olefin is a monosubstituted ethylene compound or a disubstituted ethylene compound, in which the substituents are vicinally bound to the olefinic carbon atoms, has to be provided.

E.g., 1,2 dichloroethylene may provided in step (B). This olefin may be provided as Z- or E-olefin.

Using a transition metal carbene complex such as disclosed in WO 2016/073750 for performing cross-metathesis between the products provided in step (A) and step (B) affords the respective target compound

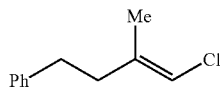

as E-isomer in excellent yield and stereoselectivity [(E)-(4-chloro-3-methylbut-3-en-1-yl)benzene; >98% conversion; 81% yield; 95:5 E:Z).

Analogously, styrene may be reacted with commercially available Z-2-bromo-butane

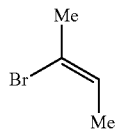

in a Heck-reaction according to step (A1) to afford the respective trisubstituted Z-ethylene compound (Z)-(3-methylpent-3-en-1-yl)benzene

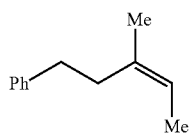

which is provided in step (A).

If 1,2 dichloroethylene is reacted with the Z-product provided in step (A) under similar conditions as above, the respective Z-target compound

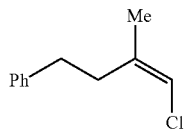 [SMILES: C/C(=C/Cl)CCc1ccccc1]

is obtained in excellent yield and stereoselectivity [(Z)-(4-chloro-3-methylbut-3-en-1-yl)benzene; >98% conversion; 86% yield; 9:91 E:Z].

In another cross-coupling embodiment, the olefin provided in step (A) may be formed by the reaction of an organo borane compound such as an organo boronic acid with a trisubstituted vinyl halide. Such reaction is known as Suzuki-coupling.

The term "trisubstituted vinyl halide" means that the vinyl halide bears three substituents including the halide-substituent.

In said trisubstituted vinyl halide, halogen and the second substituent are geminally bound to the one carbon atom of the vinyl halide and a third substituent is vicinally bound to the other olefinic carbon atom.

Accordingly, step (A) comprises step (A2):

(A2) subjecting an organo borane compound to cross-coupling with a trisubstituted vinyl halide to afford said trisubstituted ethylene compound provided in step (A).

Herein, cross-coupling takes place between carbon atom bearing the borane group of the organo borane compound and a carbon atom of the vinyl halide bearing said halide of the vinyl halide; wherein two substituents in said trisubstituted vinyl halide form the second and the third substituent of said trisubstituted ethylene compound provided in step (A); and wherein the first substituent of said formed trisubstituted ethylene compound provided in step (A) originates from said organo borane compound and replaces said halide, wherein the borane group of said organo borane compound is eliminated.

This cross-coupling reaction and the subsequent cross-metathesis reaction is exemplified by means of the following organo borane compound

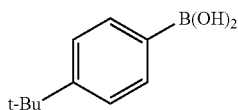 [SMILES: CC(C)(C)c1ccc(B(O)O)cc1]

which may be reacted with trisubstituted vinyl halide

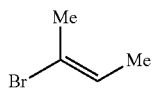

in a Suzuki-coupling according to step (A2) to afford the respective trisubstituted E-ethylene compound (E)-1-(but-2-en-2-yl)-4-(tertbutyl)benzeneyl)benzene

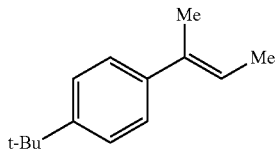 [SMILES: C/C=C(\C)c1ccc(C(C)(C)C)cc1]

which is provided in step (A).

E.g., 1,2-dichloroethylene may be provided in step (B). This olefin may be provided as Z- or E-olefin.

Using a transition metal carbene complex for performing cross-metathesis between the product provided in step (A) and step (B) affords the respective target compound

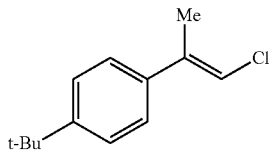 [SMILES: C/C(=C\Cl)c1ccc(C(C)(C)C)cc1]

as E-isomer in excellent yield and stereoselectivity [(E)-1-(tert-butyl)-4-(1-chloroprop-1-en-2-yl)benzene; >96% conversion; 90% yield; 98:2 E:Z].

(Z)-1-(tert-butyl)-4-(1-chloroprop-1-en-2-yl)benzene may be prepared correspondingly in >98:2 Z:E ratio starting from the respective (Z)-1-(but-2-en-2-yl)-4-(tertbutyl)benzeneyl)benzene.

In another approach, the trisubstituted ethylene compound provided in step (A) may be formed by any other reaction that provides for a trisubstituted ethylene compound.

In one embodiment, said trisubstituted ethylene compound provided in step (A) is made by the reaction of a suitable ketone with arylsulfonyl hydrazide. This reaction is known as Shapiro-reaction [see e.g. Corey, E. J., Lee, J. & Roberts, B. E. "The application of the Shapiro reaction to the stereoselective synthesis of E-trisubstituted olefins for cation-olefin cyclization by three component coupling. Tetrahedron Letters 38, 8915-8918 (1997)].

Accordingly, in one embodiment, step (A) comprises step (A3):

(A3) subjecting a ketone to arylsulfonyl hydrazide to afford said trisubstituted ethylene compound provided in step (A).

In another approach, said trisubstituted ethylene compound provided in step (A) is made by a 1,2-addition to a suitable alkyne (see e.g. Ohmura, T., Oshima, K. & Suginome, M. Palladium-catalysed cis- and trans-silaboration of terminal alkynes: Complementary access to stereo-defined trisubstituted alkenes. Chem. Commun. 1416-1418 (2008)].

Accordingly, in one embodiment, step (A) comprises step (A4):

(A4) performing a 1,2-addition to an alkyne to afford said trisubstituted ethylene compound provided in step (A);

In another approach, said trisubstituted ethylene compound provided in step (A) is made by a pericyclic reaction between an alkene bearing a hydrogen atom in an allylic position with an unsaturated compound. Such reaction type is known as Alder-ene and carbonyl-ene reaction.

Accordingly, in one embodiment, step (A) comprises step (A5):

(A5) reacting an alkene bearing a hydrogen atom in an allylic position with an unsaturated compound in a pericyclic Ene-reaction to afford said trisubstituted ethylene compound provided in step (A).

In another approach, said trisubstituted ethylene compound provided in step (A) is made by β-oxido phosphonium ylides, generated in situ from aldehydes and alkylidene (triphenyl)phosphoranes, with electrophilic halogen sources [see e.g. Hodgson, D. M. & Arif, T. Convergent and stereoselective synthesis of trisubstituted E-alkenyl bromides and iodides via β-oxido phosphonium ylides. J. Am. Chem. Soc. 130, 16500-16501 (2008)].

Accordingly, step (A) comprises step (A6):

(A6) reacting β-oxido phosphonium ylides, generated in situ from aldehydes and alkylidene(triphenyl)phosphoranes, with electrophilic halogen sources to afford said trisubstituted ethylene compound provided in step (A) in the form of E- or Z-bromo- or iodosubstituted alkenes.

In another approach, said trisubstituted ethylene compound provided in step (A) is made by monoalkylating unactivated 1,1-dichloro-1-alkenes and subsequent second substitution [see e.g. Tan, Z. & Negishi, E.-I. Widely applicable Pd-catalyzed trans-selective monoalkylation of unactivated 1,1-dichloro-1-alkenes and Pd-catalyzed second substitution for the selective synthesis of E or Z trisubstituted alkenes. Angew. Chem. Int. Ed. 45, 762-765 (2006)].

Accordingly, step (A) comprises step (A7):

(A7) monoalkylating unactivated 1,1-dichloro-1-alkenes under Pd-catalysis and subsequent Pd-catalysed second substitution to afford an E- or Z-trisubstituted ethylene compound provided in step (A).

In another approach, the trisubstituted ethylene compound provided in step (A) may be formed in the reaction of a geminal disubstituted ethylene compound with a monosubstituted ethylene compound in a cross-metathesis reaction, although such reaction may not result in stereoselectivity. As mentioned in the SUMMARY section, if necessary, the trisubstituted ethylene compound to be provided in step (A) has to be separated from side-products, e.g. from another stereoisomer in case stereoselectivity is required. However, if this separation has once been done, the trisubstituted ethylene compound provided in step (A) may be simply modified with a variety of fourth substituents originating from the monosubstituted or disubstituted ethylene compound provided in step (B).

Accordingly, step (A) may comprise step (A8):

(A8) reacting a geminal disubstituted ethylene compound with a monosubstituted ethylene compound in a cross-metathesis reaction to afford said trisubstituted ethylene compound provided in step (A).

The person skilled in the art is familiar with the reactions defined in steps (A1) to (A8) and capable of selecting the suitable starting materials in order to obtain the trisubstituted ethylene compound provided in step (A).

A further example according to the invention is presented as follows: The trisubstituted ethylene compound

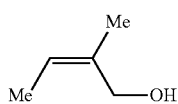

which is an allyl alcohol having Z-configuration [(Z)-2-methyl-but-2-en-1-ol] may be reacted with benzylester

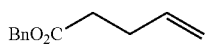

according to the method of the invention to stereoselectively afford the trisubstituted ethylene compound benzyl (Z)-6-hydroxy-5-methylhex-4-enoate

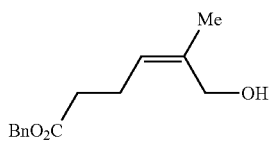

using e.g. ruthenium carbene thiocatechol complex of formula

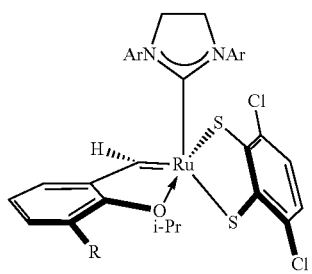

as catalyst.

The trisubstituted ethylene compound is obtained in a yield of 76% (conversion 90%) and a Z:E ratio of >98:2 if a catalyst is used in which Ar=2-F-6-Me-$C_6H_3$ and R=H.

A catalyst in which Ar=2,4,6-$Me_3$-$C_6H_2$ and R=H provides for a Z:E ratio of >98:2, a conversion of 81% and a yield of 31%. The catalysts are known from WO 2014/201300, respectively may be prepared according to methods disclosed therein.

If (E)-2-methyl-but-2-en-1-ol

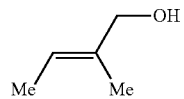

is reacted with benzylester

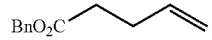

using

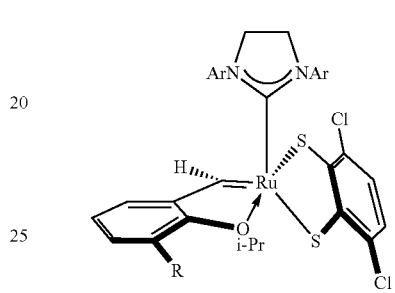

as catalyst (Ar=2-F-6-Me-$C_6H_3$ and R=H), benzyl E-6-hydroxy-5-methylhex-4-enoate

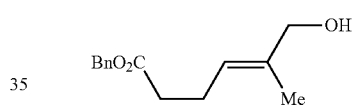

is obtained in 75% yield having an E:Z ratio of >98:2.

The above reactions verify the excellent stereoselectivity of the method according to the invention.

Exemplification of Catalysts

In one embodiment, the catalyst used in the method of the invention has the structure of the following formula II

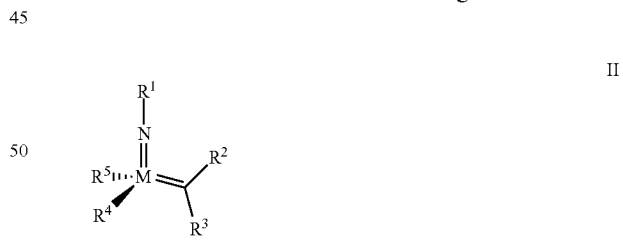

II wherein
M=Mo or W;
$R^1$ is aryl, heteroaryl, alkyl, or heteroalkyl; optionally substituted;
$R^2$ and $R^3$ can be the same or different and are hydrogen, alkyl, alkenyl, heteroalkyl, heteroalkenyl, aryl, or heteroaryl; optionally substituted;
$R^5$ is pyrrol-1-yl; 2,5-dimethyl-pyrrol-1-yl, 2,5-diphenyl-pyrrol-1-yl or halogen, halogen being preferably chlorine;
$R^4$ is a residue $R^6$—X—, wherein X=O and $R^6$ is aryl, optionally substituted;

The optional substituents may be independently selected from alkyl, preferably $C_1$-$C_4$ alkyl, such as methyl, isopropyl or t-butyl, alkoxy, preferably $C_1$-$C_4$ alkoxy, dialkylamino, preferably $N(C_1$-$C_4)_2$, phenoxy, phenyl, and halogen. Phenyl and phenoxy may in turn be optionally substituted with $C_1$-$C_4$ alkyl, $C_1$-$C_4$ alkoxy, —$N(C_1$-$C_4)_2$, phenoxy, phenyl, and halogen.

In one embodiment, $R^4$ is a residue $R^6$—X—, wherein X=O and $R^6$ is phenyl substituted with up to five substituents independently selected from alkyl, preferably $C_1$-$C_4$ alkyl, such as methyl, isopropyl or t-butyl, alkoxy, preferably $C_1$-$C_4$ alkoxy, —$N(C_1$-$C_4)_2$, phenoxy, phenyl, halogen, optionally substituted; or $R^6$ is 8-(naphthalene-1-yl)-naphthalene-1-yl, optionally substituted; or
$R^6$ is 8-phenlynaphthalene-1-yl, optionally substituted; or
$R^6$ is quinoline-8-yl, optionally substituted; or
$R^6$ is a phenyl ring which is at least substituted in 4-position with respect to O; or
$R^6$ is substituted in 2- and 4-position with respect to O; or
$R^6$ is substituted in 3- and 4-position; or
$R^6$ is substituted in 2-, 3- and 4-position; or
$R^6$ is substituted in 2-, 5- and 4-position; or
$R^6$ is substituted in 3-, 5- and 4-position; or
$R^6$ is substituted in 2-, 6- and 4-position; or
$R^6$ is substituted in 2-, 3-, 5- and 4-position; or
$R^6$ is substituted in 2-, 3-, 6- and 4-position; or
$R^6$ is substituted in 2-, 3-, 5-, 6- and 4-position.

In one embodiment, $R^2$ is —$C(CH_3)_2C_6H_5$, —$C(CH_3)_3$ or o-$C_1$-$C_4$ alkoxy-$C_6H_4$, optionally substituted, preferably with one or more of the optional substituents mentioned above, and $R^3$ is H.

In another embodiment, the catalyst used in the method of the invention has the structure of the following formula I

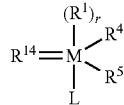

wherein:
M is Ru;
each of $R^1$ and L is independently a neutral ligand, preferably wherein $R^1$ is a nitrogen-containing heterocyclic carbene;
r is 1-3; preferably 1 or 2
each of $R^4$ and $R^5$ is independently bonded to M through a sulfur;
$R^{14}$ is a carbene;
$R^4$ and $R^5$ are taken together to form a bidentate ligand, or $R^4$ and $R^5$ are taken together with one or more of $R^1$, L and $R^{14}$ to form a polydentate ligand;
two or more of $R^1$, L and $R^{14}$ are optionally taken together to form a bidentate or polydentate ligand; and
each of $R^1$, $R^4$, $R^5$, L and $R^{14}$ is independently and optionally linked to a tag or support.

In one embodiment, the catalyst used in the method of the invention has the structure of formula I-c:

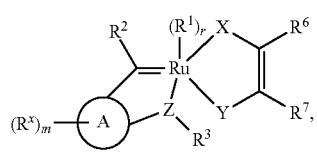

wherein:
each of $R^6$ and $R^7$ is independently R, —CN, halogen, —OR, —OC(O)R, —OSi(R)$_3$, —SR, —S(O)R, —S(O)$_2$R, —NO$_2$, —N(R')$_2$, —NR'C(O)R, —NR'C(O)OR, —NR'C(O)N(R')$_2$, —NR'SO$_2$R, —NR'SO$_2$N(R')$_2$, —NR'OR, —SeR, —Si(R)$_3$; or $R^6$ and $R^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur; or wherein the compound has the structure of formula I-d:

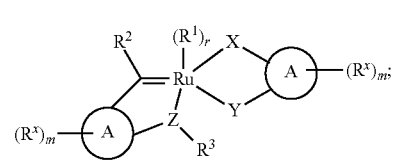

or wherein the compound has the structure of formula I-e:

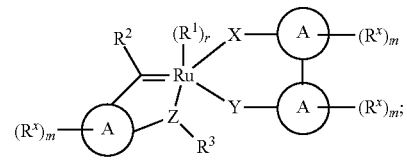

or wherein the compound has the structure of formula I-f:

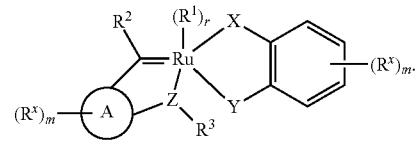

wherein
$R^1$ is a heterocyclic nitrogen-containing carbene;
r is 1;
X and Y are —S—;
Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;
each $R^x$ is independently halogen, R, —CN, —C(O)N(R')$_2$, —C(O)R, —C(O)OR, —OR, —OC(O)R, —OC(O)OR, —OC(O)N(R')$_2$, —OSi(R)$_3$, —N(R')$_2$, —N(R')$_3^+$, —NR'C(O)R, —NR'C(O)OR, —NR'C(O)N(R')$_2$, —NR'SO$_2$R, —NR'SO$_2$N(R')$_2$, —NR'OR, —NO$_2$, —Si(R)$_3$, —P(R)$_2$, —P(O)(R)$^2$, —P(O)(OR)$_2$, —SR, —SC(O)R, —S(O)R, —SO$_2$N(R')$_2$, or —SeR;
each R' is independently R, —C(O)R, —C(O)N(R)$_2$, —C(O)OR, —SO$_2$N(R)$_2$, —P(O)(OR)$_2$, or —OR; and
each R is independently hydrogen or an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;

m is 0-6;

$R^2$ is $R^x$;

$R^3$ is hydrogen or an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur; and Z is —O— or —S—.

In one embodiment, the catalyst has the structure of formula I-g

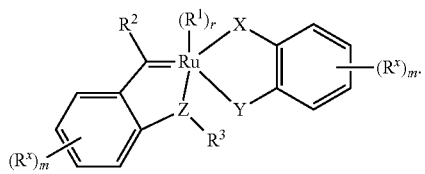

I-g wherein the substituents have the meaning as defined above.

In one embodiment, the nitrogen-containing heterocyclic carbene contains the moiety of formula 6

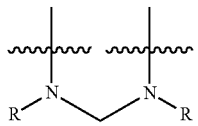

6 wherein each R is independently H, unbranched or branched $C_{1-20}$ alkyl, $C_{5-9}$ cycloalkyl, or phenyl, wherein the phenyl is optionally substituted with up to three groups independently selected from unbranched or branched $C_{1-6}$ alkyl, $C_{1-6}$ alkoxy or halogen; and wherein the chemical bonds which are symbolized with a wiggly line are connected to an optionally substituted alkenylene or alkylene group, respectively, wherein the carbene carbon atom, the two nitrogen atoms and the optionally substituted alkenylene or alkylene group form a ring.

In one embodiment, the nitrogen-containing heterocyclic carbene of formula 6 is a carbene of one of formulae 6a, 6b, 6c or 6d:

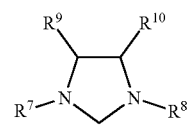

6a

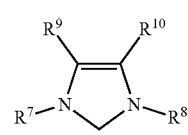

6b

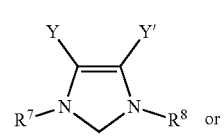

6c

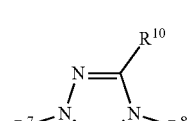

6d wherein $R^7$ and $R^8$ have the meaning of R as in formula 6, and $R^9$ and $R^{10}$ are each independently H, unbranched or branched $C_{1-20}$ alkyl, or phenyl, wherein the phenyl is optionally substituted with up to three groups independently selected from unbranched or branched $C_{1-6}$ alkyl, $C_{1-6}$ alkoxy or halogen; or $R^9$ and $R^{10}$ together with the carbon atoms to which they are attached are combined to form a carbocyclic 3 to 8 membered ring;

Y and Y' are halogen;

In another embodiment, the nitrogen-containing heterocyclic carbene contains the moiety of formula 7

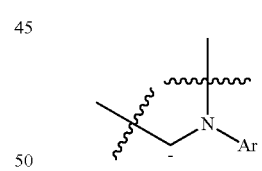

7 wherein Ar as defined in formula 7 is aryl, preferably phenyl, optionally substituted with one or more groups selected from: $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or halogen; and wherein the chemical bonds which are symbolized with a wiggly line are connected to an optionally substituted alkenylene or alkylene group, respectively, wherein the carbene carbon atom, the nitrogen atom and the optionally substituted alkenylene or alkylene group form a ring, which may optionally be bridged by an alkylene group.

In one embodiment, the heterocyclic nitrogen-containing carbene of formula 7 is a carbene of one of formulae 7a to 7k

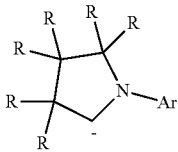

wherein each R in formula 7a is independently hydrogen, C$_1$-C$_{12}$ alkyl, C$_3$-C$_{12}$ cycloalkyl, C$_2$-C$_{12}$ alkenyl, C$_5$-C$_{20}$ aryl, C$_1$-C$_5$ perfluoroalkyl, C$_7$-C$_{24}$ aralkyl, or C$_5$-C$_{24}$ perfluoroaryl group, which are optionally substituted with at least one C$_1$-C$_{12}$ alkyl, C$_1$-C$_{12}$ perfluoroalkyl, C$_1$-C$_{12}$ alkoxy, C$_5$-C$_{24}$ aryloxy, C$_5$-C$_{20}$ heteroaryloxy, or a halogen atom; and wherein two R which are separated by the C—(CR)$_2$—C moiety can be combined with to form a cyclic system; or
is a carbene of formula 7b

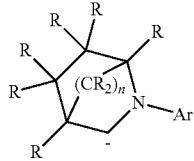

wherein each R in formula 7b is independently hydrogen, C$_1$-C$_{12}$ alkyl, or C$_3$-C$_{12}$ cycloalkyl, and n is 1, 2 or 3;
or is a carbene of formula 7c

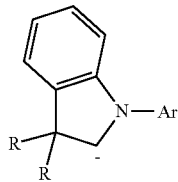

or is a carbene of formula 7d

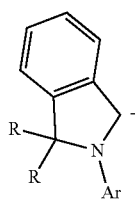

or is a carbene of formula 7e

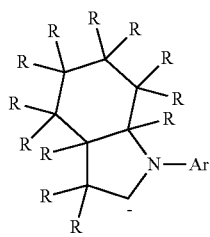

or is a carbene of formula 7f

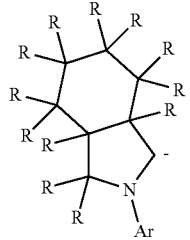

or is a camphor-derived carbene of formula 7g or 7h

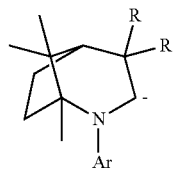

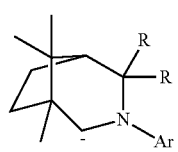

or is a carbene of formula 7i

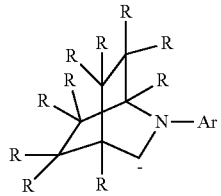

or is a carbene of formula 7k

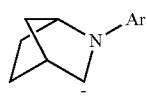

wherein each R in formulae 7c to 7i is independently hydrogen, C$_1$-C$_{12}$ alkyl, or C$_3$-C$_{12}$ cycloalkyl.

EXAMPLES

General Procedure for cross-metathesis (CM) reactions with Mo- or W-complexes: In a N$_2$-filled glove box, an oven-dried 8 mL vial equipped with a magnetic stir bar was charged with trisubstituted alkene substrate and the corresponding disubstituted alkene substrate such as Z-1,2-dichloroethene or E-1,2-dichloroethene. A solution of the catalyst in benzene was then added. The resulting mixture was allowed to stir for 4 h at 22° C., after which the reaction was quenched by the addition of wet (undistilled) CDCl$_3$ (percent conversion was determined by $^1$H NMR analysis of the unpurified mixture). Purification was performed through silica gel chromatography and/or preparative thin layer chromatography.

Example 1: (E)-(4-chloro-3-methylbut-3-en-1-yl)benzene

Following the general procedure, a solution of Mo-carbene complex [(C$_6$F$_5$N)Mo(CMe$_2$Ph)(Me$_2$Py)(O-2,6(2,4,6-Et$_3$Ph)$_2$C$_6$H$_3$)] [Koh, M. J., Nguyen, T. T., Zhang, H., Schrock, R. R., Hoveyda, A. H. Nature 531, 459-465 (2016)] in benzene (0.1 M, 10 µL, 1.0 µmol) was transferred by syringe to an oven-dried vial containing E-1,2-dichloroethene (48.5 mg, 0.500 mmol) and (E)-(3-methylpent-3-en-1-yl)benzene (16.0 mg, 0.100 mmol). The resulting solution was allowed to stir for 4 h at 22° C. The reaction was quenched by addition of wet CDCl$_3$ and analysis of the unpurified mixture revealed 98% consumption of (E)-(3-methylpent-3-en-1-yl)benzene. The resulting orange oil was purified by silica gel chromatography (100% pentane) to afford the product (14.6 mg, 0.0808 mmol, 81% yield) in 95:5 E:Z ratio as colorless oil. IR (neat): 3064 (w), 2926 (w), 2855 (w), 1641 (w), 1602 (w), 1454 (m), 1030 (m); $^1$H NMR (400 MHz, CDCl$_3$): δ 7.32-7.26 (2H, m), 7.23-7.18 (1H, m), 7.18-7.14 (2H, m), 5.81-5.78 (1H, m), 2.77-2.71 (2H, m), 2.40-2.34 (2H, m), 1.83 (3H, d, J=1.4 Hz); $^{13}$C NMR (100 MHz, CDCl$_3$): δ 141.4, 138.2, 128.6, 128.5, 126.2, 112.8, 39.2, 34.4, 16.8; HRMS [M+H]+ calcd for C$_{11}$H$_{14}$Cl: 181.0784, found: 181.0785.

Example 2: (Z)-(4-chloro-3-methylbut-3-en-1-yl)benzene

Following the general procedure, a solution of the same catalyst as used in Example 1 in benzene (0.1 M, 15 µL, 1.5 µmol) was transferred by syringe to an oven-dried vial containing Z-1,2-dichloroethene (24.3 mg, 0.500 mmol) and (Z)-(3-methylpent-3-en-1-yl)benzene (8.0 mg, 0.0500 mmol). The resulting solution was allowed to stir for 4 h at 22° C. The reaction was quenched by addition of wet CDCl$_3$ and analysis of the unpurified mixture revealed 98% consumption of (Z)-(3-methylpent-3-en-1-yl)benzene. The resulting orange oil was purified by silica gel chromatography (100% pentane) to afford the product (7.8 mg, 0.0432 mmol, 86% yield) in 91:9 Z:E ratio as colorless oil. IR (neat): 3027 (w), 2929 (w), 2859 (w), 1603 (w), 1494 (m), 1433 (m), 1031 (m), 741 (s), 700 (s); $^1$H NMR (400 MHz, CDCl$_3$): E-isomer (major): δ 7.34-7.14 (5H, m), 5.80 (1H, dt, J=1.5, 0.7 Hz), 2.79-2.68 (2H, m), 2.55-2.46 (2H, m), 1.74 (3H, d, J=1.6 Hz); $^{13}$C NMR (100 MHz, CDCl$_3$): δ 141.7, 138.2, 128.5, 128.5, 126.1, 112.3, 34.0, 33.2, 21.2.

Example 3: (E)-1-(tert-butyl)-4-(1-chloroprop-1-en-2-yl)benzene

Following the general procedure, a solution of Mo-carbene complex [(C$_6$F$_5$N)Mo(CMe$_2$Ph)(Me$_2$Py)(O-2,6(3,5-(t-Bu)$_2$Ph)$_2$C$_6$H$_3$)] [Nguyen, T. T., Koh, M. J., Shen, X., Romiti, F., Schrock, R. R., Hoveyda, A. H. Science 552, 569-575 (2016)] in benzene (0.1 M, 15 µL, 1.5 µmol) was transferred by syringe to an oven-dried vial containing Z-1,2-dichloroethene (24.2 mg, 0.250 mmol) and (E)-1-(but-2-en-2-yl)-4-(tertbutyl)benzene (9.4 mg, 0.0499 mmol). The resulting solution was allowed to stir for 4 h at 22° C. The reaction was quenched by addition of wet CDCl$_3$ and analysis of the unpurified mixture revealed >98% consumption of (E)-1-(but-2-en-2-yl)-4-(tert-butyl)benzene. The resulting orange oil was purified by silica gel chromatography (100% pentane) to afford the product (9.4 mg, 0.0450 mmol, 90% yield) in >98:2 E:Z ratio as colorless oil. IR (neat): 3034 (w), 2962 (m), 2867 (w), 1620 (w), 1363 (m), 1245 (m), 1114 (m), 985 (m); $^1$H NMR (400 MHz, CDCl3): δ 7.38-7.34 (2H, m), 7.30-7.26 (2H, m), 6.32-6.30 (1H, m), 2.20-2.19 (3H, m), 1.33 (9H, s); $^{13}$C NMR (100 MHz, CDCl$_3$): δ 151.0, 138.4, 137.5, 125.7, 125.6, 115.3, 34.7, 31.4, 16.9; HRMS [M+H]+ calcd for C$_{13}$H$_{18}$Cl: 209.1097, found: 209.1102.

Example 4: (Z)-1-(tert-butyl)-4-(1-chloroprop-1-en-2-yl)benzene

Following the general procedure, a solution of the same complex as in Example 3 in benzene (0.1 M, 25 µL, 2.5 µmol) was transferred by syringe to an oven-dried vial containing Z-1,2-dichloroethene (24.3 mg, 0.251 mmol) and (E)-1-(but-2-en-2-yl)-4-(tertbutyl)benzene (9.4 mg, 0.0500 mmol). The resulting solution was allowed to stir for 4 h at 22° C. The reaction was quenched by addition of wet CDCl$_3$ and analysis of the unpurified mixture revealed 86% consumption of starting material. The resulting red oil was purified by silica chromatography (100% hexanes) to afford Z-3b (6.8 mg, 0.0326 mmol, 65% yield) in >98:2 Z:E ratio as clear colorless oil. IR (neat): 2962 (m), 2868 (w), 1509 (m), 1463 (w), 1438 (w), 1400 (w), 1363 (m), 1269 (m), 1114 (m), 1014 (m), 838 (s), 788 (m), 587 (s); $^1$H NMR (400 MHz, CDCl$_3$): δ 7.42-7.38 (2H, m), 7.36-7.32 (2H, m), 6.10 (1H, q, J=1.6 Hz), 2.09 (3H, d, J=1.6 Hz), 1.34 (9H, s); $^{13}$C NMR (100 MHz, CDCl$_3$) δ 150.7, 137.8, 135.7, 127.7, 125.2, 112.3, 34.8, 31.5, 23.5; HRMS [M+H]+ calcd for C$_{13}$H$_{18}$Cl: 209.1097, found: 209.1099.

General procedure for cross-metathesis with Ru catecho-thiolate complexes: In a N$_2$-filled glovebox, an oven-dried vial equipped with a magnetic stir bar was charged with alkene substrates and a THF solution of the Ru-complex. The vessel was sealed and the mixture was allowed to stir at 22° C. for 1 h. The volatiles were then removed in vacuo (100 torr for 2 mins). The flask containing the residue was then charged with the trisubstituted alkene substrate, followed by the addition of a solution of the Ru-complex in THF, and the mixture was subjected to reduced pressure (100 torr) for 1 hour, and the resulting solution was allowed to stir for 15 h at 22° C. At this point, the reaction was quenched by the addition of wet (undistilled) Et$_2$O while being exposed to air. The volatiles were subsequently removed in vacuo, and the resulting residue (typically black oil) was purified by silica gel chromatography and filtered through a small plug of activated charcoal.

Example 5: Benzyl (Z)-6-hydroxy-5-methylhex-4-enoate

Following the general procedure, in a N$_2$-filled glovebox, an oven-dried vial equipped with a magnetic stir bar was charged with benzyl pent-4-enoate (9.5 mg, 0.05 mmol) and a THF solution of Z-butene (in order to prevent degradation of the complex) (13 wt %, 107 mg, 0.25 mmol), this was followed by addition of a THF solution (200 µL) of the Ru-complex (Ar=2-F-6-Me-C$_6$H$_3$ and R=H)

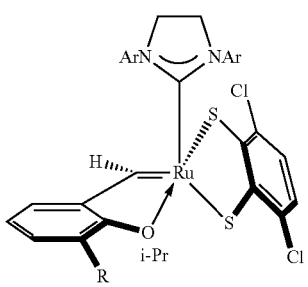

(0.38 mg, 0.0005 mmol). The vessel was then sealed. The mixture was allowed to stir at 22° C. for 1 h, after which the volatiles were removed in vacuo (100 torr, 2 min). The vessel was then charged with (in this precise order) (Z)-2-methylbut-2-en-1-ol (21.5 mg, 0.25 mmol), a solution of the Ru-complex (1.9 mg, 0.0025 mmol in 200 μL THF) and subjected to 100 torr vacuum for 1 h. The resulting solution was allowed to stir at 22° C. for 15 h. At this point, the reaction was quenched by the addition of wet (undistilled) $Et_2O$ while being exposed to air, and the volatiles were removed in vacuo. The resulting black oil was purified by silica gel chromatography (20~50% ethyl ether in hexanes) and filtered through a small plug of activated charcoal to afford benzyl (Z)-6-hydroxy-5-methylhex-4-enoate in >98:2 Z:E ratio as colorless oil (8.7 mg, 0.037 mmol, 74% yield). IR (neat): 3410 (br, m), 2966 (m), 2942 (m), 1732 (s), 1454 (w), 1416 (m), 1381 (m), 1351 (m), 1259 (m), 1213 (m), 1145 (m), 1003 (m), 950 (m), 750 (m), 698 (m) cm-1; $^1H$ NMR (600 MHz, $CDCl_3$): δ 7.41-7.30 (m, 5H), 5.21 (t, J=7.2 Hz, 1H), 5.11 (s, 2H), 4.10 (d, J=4.8 Hz, 2H), 2.49-2.35 (m, 4H), 1.93 (t, J=5.3 Hz, 1H), 1.78 (s, 3H); $^{13}C$ NMR (150 MHz, $CDCl^3$): δ 173.6, 136.8, 136.0, 128.7, 128.4, 128.4, 126.0, 66.5, 61.6, 34.2, 23.1, 21.8; HRMS[M+H]+: Calcd for $C_{14}H_{19}O_3$: 235.1334, found: 235.1345.

Example 6: Benzyl (E)-6-hydroxy-5-methylhex-4-enoate

Following the general procedure, in a $N_2$-filled glovebox, an oven-dried vial equipped with a magnetic stir bar was charged with benzyl pent-4-enoate (9.5 mg, 0.05 mmol) and a THF solution of Z-butene (in order to prevent degradation of the complex) (13 wt %, 107 mg, 0.25 mmol), this was followed by addition of a THF solution (200 μL) of the ruthenium complex as in Example 5 (0.38 mg, 0.0005 mmol). The vessel was then sealed. The mixture was allowed to stir at 22° C. for 1 h, after which the volatiles were removed in vacuo (100 torr, 2 min). The vessel was then charged with (in this precise order) (E)-2-methylbut-2-en-1-ol (21.5 mg, 0.250 mmol), a solution of the catalyst (1.9 mg, 0.0025 mmol in 200 μL THF) and subjected to 100 torr vacuum for 1 h. The resulting solution was allowed to stir at 22° C. for 15 h. At this point, the reaction was quenched by the addition of wet (undistilled) $Et_2O$ while being exposed to air, and the volatiles were removed in vacuo. The resulting black oil was purified by silica gel chromatography (20~50% ethyl ether in hexanes) and filtered through a small plug of activated charcoal to afford benzyl (E)-6-hydroxy-5-methylhex-4-enoate in >98:2 E:Z ratio as colorless oil (8.5 mg, 0.035 mmol, 75% yield). IR (neat): 3372 (br, m), 3030 (w), 2918 (m), 2855 (m), 1731 (s), 1497 (m), 1454 (m), 1417 (m), 1381 (m), 1260 (m), 1212 (m), 1146 (s), 1065 (m), 1004 (m), 804 (m), 750 (m), 697 (m) cm-1; $^1H$ NMR (600 MHz, $CDCl_3$): δ 7.38-7.32 (m, 5H), 5.38 (t, J=6.4 Hz, 1H), 5.12 (s, 2H), 3.97 (s, 2H), 2.47-2.33 (m, 4H), 1.62 (br, 4H); $^{13}C$ NMR (150 MHz, $CDCl_3$): δ 173.2, 136.5, 136.2, 128.7, 128.4, 128.4, 123.7, 68.7, 66.4, 34.2, 23.3, 13.8; HRMS[M+H−H2O]+: Calcd for C14H17O2: 217.1229, found: 217.1231.

The invention claimed is:

1. A method of forming a trisubstituted ethylene compound, the method comprising:
    (A) providing a trisubstituted ethylene compound bearing a first substituent, a second substituent and a third substituent, in which the first substituent and the second substituent are bound to the one olefinic carbon atom, wherein said first substituent and said second substituent are different from one another, and wherein said third substituent is bound to the other olefinic carbon atom;
    (B) providing an olefin bearing at least a fourth substituent, which is bound to an olefinic carbon atom, wherein said fourth substituent is different from the third substituent of the trisubstituted ethylene compound provided in step (A); and wherein said olefin is a monosubstituted ethylene compound or a disubstituted ethylene compound in which the substituents are vicinally bound to the olefinic carbon atoms, optionally wherein the substituents are identical;
    (C) subjecting the trisubstituted ethylene compound provided in step (A) to a cross-metathesis reaction with the olefin provided in step (B) to form said trisubstituted ethylene, wherein the formed trisubstituted ethylene compound has one olefinic carbon atom from the trisubstituted ethylene compound provided in step (A), which bears said first substituent and said second substituent, and one olefinic carbon atom from the olefin provided in step (B), which bears said fourth substituent;
    wherein the cross-metathesis reaction is catalysed by a transition metal complex bearing ligands from which one ligand is a carbene ligand, wherein the metal complex is characterized by a M=C moiety, wherein M is the transition metal and C is the carbene carbon atom of the carbene ligand.

2. The method of claim 1, wherein said third substituent is a $C_{1-4}$-alkyl residue.

3. The method of claim 1, wherein said third substituent is a methyl group.

4. The method of claim 1, wherein at least one of the first substituent, the second substituent and the fourth substituent is a functional group or comprises a functional group.

5. The method of claim 1, wherein the transition metal is selected from Mo, W or Ru.

6. The method of claim 1, wherein the carbon atom of the carbene complex is substituted with hydrogen or hydrogen and a residue selected from alkyl, optionally substituted, or aryl, optionally substituted with one or more of $C_{1-4}$ alkyl, $C_{1-4}$ alkoxy, halogen, nitro, —C(O)—N($C_{1-4}$ alkyl)$_2$, —S(O)$_2$—N($C_{1-4}$ alkyl)$_2$, —NH—C(O)($C_{1-4}$ alkyl) or $CF_3$.

7. The method of claim 1, wherein the M=C moiety is selected from M=CH$_2$, M=C(H)(t-Bu), M=C(H)(CMe$_2$C$_6$H$_5$), M=C(H)(C$_6$H$_5$), M=C(H)(o-(C$_{1-4}$ alkoxy)C$_6$H$_4$), wherein the C$_6$H$_4$ group of the M=C(H)(o-(C$_{1-4}$ alkoxy)C$_6$H$_4$) moiety is optionally substituted with one or more of $C_{1-4}$ alkyl, $C_{1-4}$ alkoxy, halogen, nitro, —C(O)—N($C_{1-4}$ alkyl)$_2$, —S(O)$_2$—N($C_{1-4}$ alkyl)$_2$, —NH—C(O)($C_{1-4}$ alkyl) or $CF_3$.

8. The method of claim 1, wherein the trisubstituted ethylene compound provided in step (A) is a Z-olefin and the trisubstituted ethylene compound formed in step (C) is a Z-olefin or the trisubstituted ethylene compound provided in step (A) is an E-olefin and the trisubstituted ethylene compound formed in step (C) is an E-olefin.

9. The method of claim 8, wherein the stereoselectivity of the cross-metathesis reaction is more than 90%.

10. The method of claim 1, wherein step (A) comprises one of the following steps (A1) to (A8):
   (A1) subjecting an olefin containing at least one olefinic hydrogen to cross-coupling with an unsaturated halide or triflate to afford said trisubstituted ethylene compound provided in step (A);
   (A2) subjecting an organo borane compound to cross-coupling with a trisubstituted vinyl halide to afford said trisubstituted ethylene compound provided in step (A);
   (A3) reacting a ketone with arylsulfonyl hydrazide to afford said trisubstituted ethylene compound provided in step (A);
   (A4) performing an 1,2-addition to an alkyne to afford said trisubstituted ethylene compound provided in step (A);
   (A5) reacting an alkene bearing a hydrogen atom in an allylic position with an unsaturated compound in a pericyclic Ene-reaction to afford said trisubstituted ethylene compound provided in step (A);
   (A6) reacting β-oxido phosphonium ylides, generated in situ from aldehydes and alkylidene(triphenyl)phosphoranes, with electrophilic halogen sources to afford said trisubstituted ethylene compound provided in step (A) in the form of E- or Z-bromo- or iodosubstituted alkenes;
   (A7) monoalkylating unactivated 1,1-dichloro-1-alkenes under Pd-catalysis and subsequent Pd-catalysed second substitution to afford an E- or Z-trisubstituted ethylene compound provided in step (A);
   (A8) reacting a geminal disubstituted ethylene compound bearing the first substituent and the second substituent with a monosubstituted ethylene compound bearing the third substituent in a cross-metathesis reaction to afford said trisubstituted ethylene compound provided in step (A).

11. The method of claim 1, wherein the catalyst has the structure of formula II

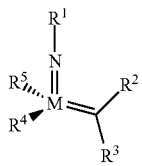

wherein
M=Mo or W;
$R^1$ is aryl, heteroaryl, alkyl, or heteroalkyl; optionally substituted;
$R^2$ and $R^3$ can be the same or different and are hydrogen, alkyl, alkenyl, heteroalkyl, heteroalkenyl, aryl, or heteroaryl; optionally substituted;
$R^5$ is pyrrol-1-yl; 2,5-dimethyl-pyrrol-1-yl, 2,5-diphenyl-pyrrol-1-yl or halogen;
$R^4$ is a residue $R^6$—X—, wherein X=O and $R^6$ is aryl, optionally substituted;
wherein the optional substituents may be independently selected from alkyl, alkoxy, phenoxy, phenyl, and halogen, wherein phenyl is in turn optionally substituted with $C_1$-$C_4$ alkyl, $C_1$-$C_4$ alkoxy, phenoxy, phenyl, —N($C_1$-$C_4$ alkyl)$_2$ or halogen.

12. The method of claim 11, wherein $R^2$ is —C(CH$_3$)$_2$C$_6$H$_5$, —C(CH$_3$)$_3$ or o-$C_1$-$C_4$ alkoxy-C$_6$H$_4$, optionally substituted, and $R^3$ is H.

13. The method of claim 1, wherein the catalyst has the structure of formula I

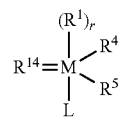

wherein:
M is Ru;
each of $R^1$ and L is independently a neutral ligand, and wherein $R^1$ is a nitrogen-containing heterocyclic carbene;
r is 1-3;
each of $R^4$ and $R^5$ is independently bonded to M through a sulfur;
$R^{14}$ is a carbene;
$R^4$ and $R^5$ are taken together to form a bidentate ligand, or $R^4$ and $R^5$ are taken together with one or more of $R^1$, L and $R^{14}$ to form a polydentate ligand;
two or more of $R^1$, L and $R^{14}$ are optionally taken together to form a bidentate or polydentate ligand; and
each of $R^1$, $R^4$, $R^5$, L and $R^{14}$ is independently and optionally linked to a tag or support.

14. The method of claim 13, wherein the catalyst has the structure of formula I-c:

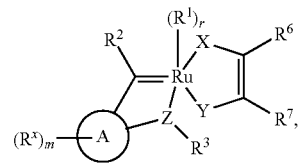

wherein:
each of $R^6$ and RT is independently R, —CN, halogen, —OR, —OC(O)R, —OSi(R)$_3$, —SR, —S(O)R, —S(O)$_2$R, —NO$_2$, —N(R')$_2$, —NR'C(O)R, —NR'C(O)OR, —NR'C(O)N(R')$_2$, —NR'SO$_2$R, —NR'SO$_2$N(R')$_2$, —NR'OR, —SeR, —Si(R)$_3$; or $R^6$ and RT are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur; or
the structure of formula I-d:

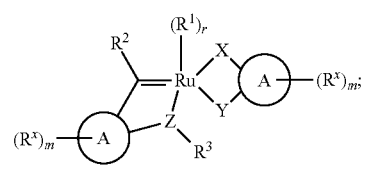

or the structure of formula I-e:

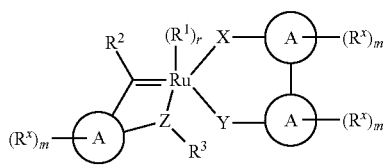

I-e or the structure of formula I-f:

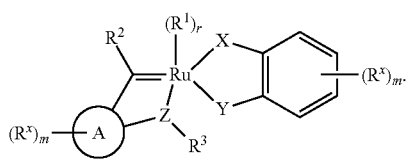

I-f wherein
r is 1;
X and Y are —S—;
Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;
each $R^x$ is independently halogen, R, —CN, —C(O)N(R')$_2$, —C(O)R, —C(O)OR, —OR, —OC(O)R, —OC(O)OR, —OC(O)N(R')$_2$, —OSi(R)$_3$, —N(R')$_2$, —N(R')$_3$+, —NR'C(O)R, —NR'C(O)OR, —NR'C(O)N(R')$_2$, —NR'SO$_2$R, —NR'SO$_2$N(R')$_2$, —NR'OR, —NO$_2$, —Si(R)$_3$, —P(R)$_2$, —P(O)(R)$_2$, —P(O)(OR)$_2$, —SR, —SC(O)R, —S(O)R, —SO$_2$R, —SO$_3$R, —SO$_2$N(R')$_2$, or —SeR;
each R' is independently R, —C(O)R, —C(O)N(R)$_2$, —C(O)OR, —SO$_2$R, —SO$_2$N(R)$_2$, —P(O)(OR)$_2$, or —OR; and
each R is independently hydrogen or an optionally substituted group selected from C$_{1-20}$ aliphatic, C$_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:
two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;
m is 0-6;

$R^2$ is $R^x$;
$R^3$ is hydrogen or an optionally substituted group selected from C$_{1-20}$ aliphatic, C$_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur; and
Z is —O— or —S—.

15. The method of claim 13, wherein the catalyst has the structure of formula I-g:

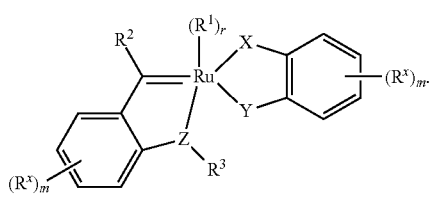

I-g

16. The method of claim 13, wherein the nitrogen-containing heterocyclic carbene contains the moiety of formula 6

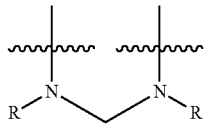

6 wherein each R is independently H, unbranched or branched C$_{1-20}$ alkyl, C$_{5-9}$ cycloalkyl, or phenyl, wherein the phenyl is optionally substituted with up to three groups independently selected from unbranched or branched C$_{1-6}$ alkyl, C$_{1-6}$ alkoxy or halogen; and
wherein the chemical bonds which are symbolized with a wiggly line are connected to an optionally substituted alkenylene or alkylene group, respectively, wherein the carbene carbon atom, the two nitrogen atoms and the optionally substituted alkenylene or alkylene group form a ring.

17. The method of claim 16, wherein the nitrogen-containing heterocyclic carbene of formula 6 is a carbene of one of formulae 6a, 6b, 6c or 6d:

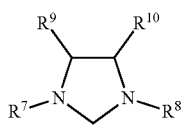

6a

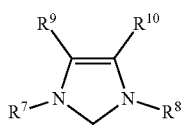

6b

-continued

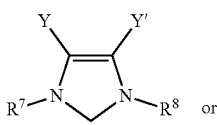

6c or

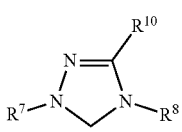

6d wherein R⁷ and R⁸ have the meaning of R as in formula 6, and R⁹ and R¹⁹ are each independently H, unbranched or branched $C_{1-20}$ alkyl, or phenyl, wherein the phenyl is optionally substituted with up to three groups independently selected from unbranched or branched $C_{1-6}$ alkyl, $C_{1-6}$alkoxy or halogen; or R⁹ and R¹⁹ together with the carbon atoms to which they are attached are combined to form a carbocyclic 3 to 8 membered ring;

Y and Y' are halogen.

18. The method of claim 13, wherein the nitrogen-containing heterocyclic carbene contains the moiety of formula 7

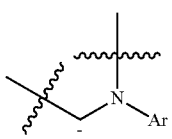

7 wherein Ar as defined in formula 7 is aryl, optionally substituted with one or more groups selected from: $C_1$-$C_{12}$ alkyl, $C_1$-$C_{12}$ perfluoroalkyl, $C_1$-$C_{12}$ alkoxy, $C_5$-$C_{24}$ aryloxy, and $C_5$-$C_{20}$ heteroaryloxy group, or halogen; and wherein the chemical bonds which are symbolized with a wiggly line are connected to an optionally substituted alkenylene or alkylene group, respectively, wherein the carbene carbon atom, the nitrogen atom and the optionally substituted alkenylene or alkylene group form a ring, which may optionally be bridged by an alkylene group.

19. The method of claim 18, wherein the heterocyclic nitrogen-containing carbene of formula 7 is a carbene of one of formulae 7a to 7k

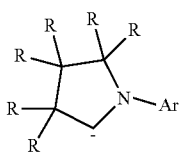

7a wherein each R in formula 7a is independently hydrogen, $C_1$-$C_{12}$ alkyl, $C_3$-$C_{12}$ cycloalkyl, $C_2$-$C_{12}$ alkenyl, $C_5$-$C_{20}$ aryl, $C_1$-$C_5$ perfluoroalkyl, $C_7$-$C_{24}$ aralkyl, or $C_5$-$C_{24}$ perfluoroaryl group, which are optionally substituted with at least one $C_1$-$C_{12}$ alkyl, $C_{12}$ perfluoroalkyl, $C_1$-$C_{12}$ alkoxy, $C_5$-$C_{24}$ aryloxy, $C_5$-$C_{20}$ heteroaryloxy, or a halogen atom; and wherein two R which are separated by the C—(CR)₂—C moiety can be combined with to form a cyclic system; or is a carbene of formula 7b

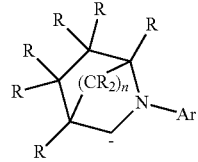

7b wherein each R in formula 7b is independently hydrogen, $C_1$-$C_{12}$ alkyl, or $C_3$-$C_{12}$ cycloalkyl, and n is 1, 2 or 3; or is a carbene of formula 7c

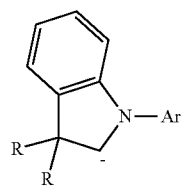

7c or is a carbene of formula 7d

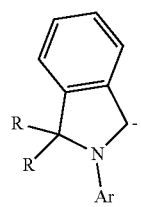

7d or is a carbene of formula 7e

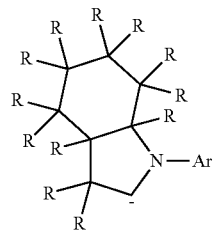

7e or is a carbene of formula 7f

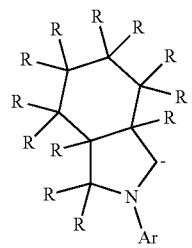

7f or is a camphor-derived carbene of formula 7g or 7h
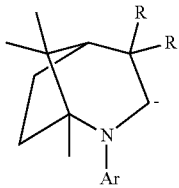
7g
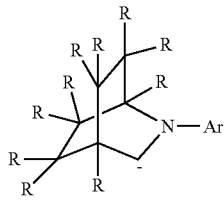
7h
or is a carbene of formula 7i
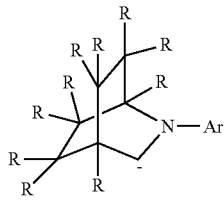
7i
or is a carbene of formula 7k
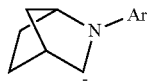
7k
wherein each R in formulae 7c to 7i is independently hydrogen, $C_1$-$C_{12}$ alkyl, or $C_3$-$C_{12}$ cycloalkyl.
* * * * *

UNITED STATES PATENT AND TRADEMARK OFFICE
CERTIFICATE OF CORRECTION

PATENT NO. : 11,332,426 B2
APPLICATION NO. : 16/646479
DATED : May 17, 2022
INVENTOR(S) : Amir H. Hoveyda et al.

It is certified that error appears in the above-identified patent and that said Letters Patent is hereby corrected as shown below:

In the Claims

Column 24, Line 46 reads, "...RT is independently" which should read, "...$R^7$ is independently"

Column 24, Line 50 reads, "...or $R^6$ and RT are" which should read, "...or $R^6$ and $R^7$ are"

Column 27, Line 17 reads, "...$R^9$ and $R^{19}$" which should read, "...$R^9$ and $R^{10}$"

Column 27, Line 22 reads, "...$R^9$ and $R^{19}$" which should read, "...$R^9$ and $R^{10}$"

Column 27, Line 67 reads, "...$C_{12}$ perfluoroalkyl" which should read, "... $C_1$-$C_{12}$ perfluoroalkyl"

Signed and Sealed this
Twenty-first Day of March, 2023

Katherine Kelly Vidal
*Director of the United States Patent and Trademark Office*